US 6,732,737 B1

(12) United States Patent
Brown

(10) Patent No.: US 6,732,737 B1
(45) Date of Patent: May 11, 2004

(54) ULTIMATE LIP GUARD U.V. SUN PROTECTOR

(76) Inventor: Charles B. Brown, 2309 State Hwy. 304, Ten Mile, TN (US) 37880

( * ) Notice: Subject to any disclaimer, the term of this patent is extended or adjusted under 35 U.S.C. 154(b) by 0 days.

(21) Appl. No.: 10/448,349

(22) Filed: May 30, 2003

(51) Int. Cl.[7] .................................................. A61F 11/00

(52) U.S. Cl. ....................................... 128/857; 128/859

(58) Field of Search .................................. 128/846, 848, 128/857, 858, 859–861; 602/902

(56) References Cited

U.S. PATENT DOCUMENTS

| 4,495,945 A | * | 1/1985 | Liegner | 128/200.26 |
| 5,165,423 A | * | 11/1992 | Fowler | 128/861 |
| 5,669,395 A | * | 9/1997 | Thompson | 128/846 |
| 5,899,206 A | * | 5/1999 | Reynolds | 128/857 |

* cited by examiner

Primary Examiner—Michael A. Brown
(74) Attorney, Agent, or Firm—John B. Dickman, III

(57) ABSTRACT

This invention sets forth a protective device for the lips of a person who may be exposed to the sun, wind or a tanning bed and the like, in their jobs or in relaxing at the seashore, boating, sunbathing and the like, and is inexpensive, easy to apply and remove and can be carried in a pocket or purse.

5 Claims, 1 Drawing Sheet

ULTIMATE LIP GUARD U.V. SUN PROTECTOR

BACKGROUND OF THE INVENTION

This invention relates to a lip protection device for shielding a user's lips from damage by sun rays; in particular, a lip protection device which covers the entire lip area and is held in place by biting on an extension, said extension having breathing tubes incorporated therein.

Sun exposure presents several severe problems to a person's lips such as blistering, chapping or cracking. Lip damage often occurs when sun bathing or some other sun related activity, such as skiing, golfing, hiking, or tanning bed use. Activities like those listed where a person's attention is focused may cause the person not to take proper protection from the sun. Everyone is aware of sunburn to the skin which can result in cancer, but few people pay attention to their lips. Yet, sun damage can cause major discomfort from blistering, chapping or cracking that can require days or weeks of medication, not to mention spending time out of the sun.

SUMMARY OF THE INVENTION

In accordance with the invention, a molded plastic device of either a hard or soft plastic is the same shape of lips that is treated to repel ultra-violet rays from the sun. To keep the lip protection device in place, the molded lips include an integral protrusion that extends into a user's mouth where is held in place between the teeth. Breathing tubes are provided in the protrusion so the user can breathe through his/or her mouth without removing the protection device. The inner flange of the mouthpiece does not have to be used primarily for biting purposes. Individuals who have a tooth overbite would need less flange so therefor the inner flange could be shortened or modified to set on the outer part of an individuals teeth as well. The plastic may be a polycarbon or other suitable material.

DESCRIPTION OF THE INVENTION

Figure 1:
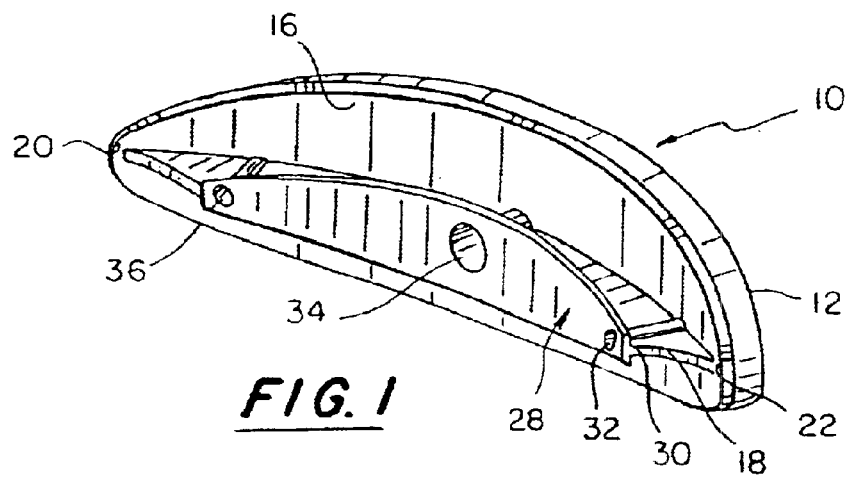
FIG. 1 is a perspective view of a lip protection device of the invention.
Figure 2:
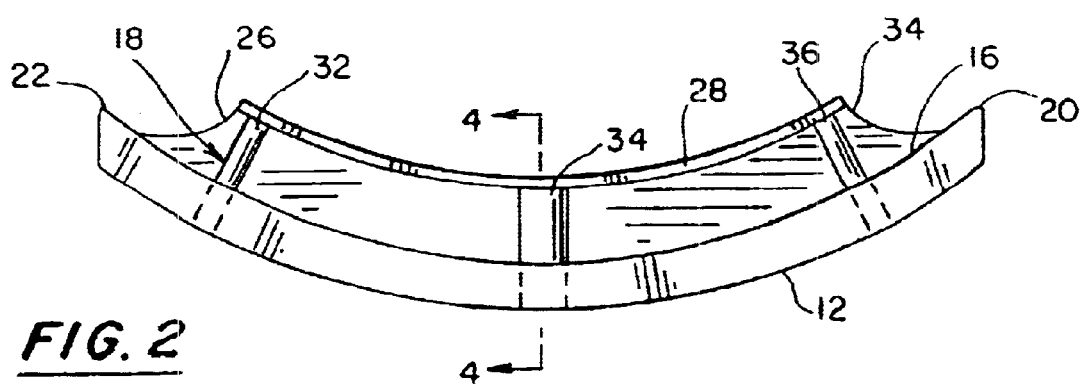
FIG. 2 is a top view of a lip protection device of FIG. 1.
Figure 3:
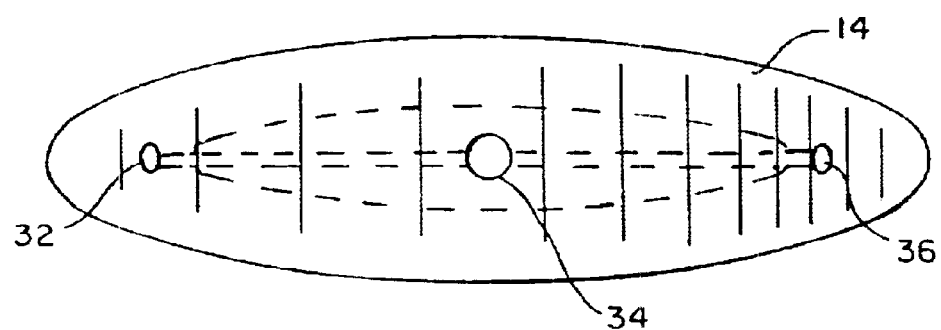
FIG. 3 is a front view of a lip protection device of FIG. 1.

Referring to the drawings, FIGS. 1 to 4, there is shown a lip protection device 10 of the invention. There is an exterior section 12 for covering the lips. FIG. 2 shows the front surface 14 with an oval shape to cover both the upper and the lower lips. Front surface 14 is treated or impregnated with an ultra-violet ray-blocking agent. There are several such agents that are available for such purposes. Looking at FIG. 2, it can be seen that the exterior section 12 has a curved shape to conform to a user's mouth and a backside 16 completes the lip protection portion of the device.

Figure 4:
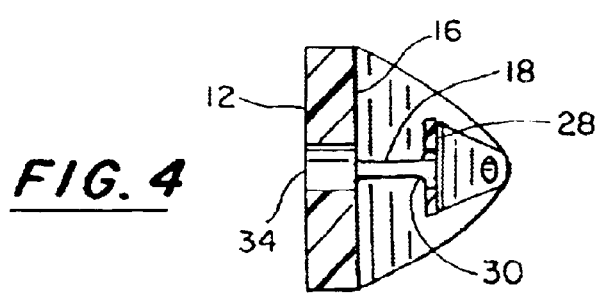
FIG. 4 is a cross-section view taken along the line 4—4 of FIG. 2.

Extending from the backside 16 or the side pressed against a user's lips, is an integral protrusion 18. A user will bite down on protrusion 18 to hold the lip protection device 10 against the lips, covering them to avoid the sun's rays. Protrusion 18 extends from a place near edge 20 to a place near edge 22, with a pair of arcuate ends 24 and 26 protrusion 18 comfortably fits against the corners of a user's mouth. To make it easier to hold the protection device 10 in a user's mouth, protrusion 18 has a stop 28 which extends across the protrusion's back end 30, as seen in FIGS. 2 and 4. Stop 28 is integral with the protrusion 18 and is parallel to the backside 16 of the lip protection portion of the device 10.

Breathing apertures 32, 34 and 36 extend through the exterior surface 12, backside 16, protrusion 18 and stop 28 permitting a user to breathe without exposing the lips.

There is one embodiment of the invention, however one skilled in the art may realize other embodiments. One should look at the claims, description and drawings to understand the scope of the invention.

What is claimed:

1. A lip protection device to shield and protect a user's lips against sun damage comprising:

an oval shaped lip covering member having ultra-violet ray blocking properties, where said oval shaped lip covering member extends beyond a user's lips for total coverage;

said oval shaped lip cover member having a front side and a back side where said back side is integrally connected to a protrusion which extends into a user's mouth to hold said lip protection device in place by biting on said protrusion;

said oval shaped lip covering member having a pair of ends where said protrusion having a pair of arcuate ends blends into said backside short of said outer edges of said oval shaped lip covering member where said arcuate ends comfortably fit against the corners of a user's mouth;

a stop member integral with said protrusion connected to and spaced from said backside of said oval shaped lip covering member, where said stop member aids in said lip protection device in place; and, a plurality of apertures extending through said oval shaped lip covering member, said protrusion and said stop member where a user is able to breathe without removing said lip protection device.

2. A lip protection device as in claim 1 where said lip protection device is molded of a hard plastic material, such as polycarbon or other plastics.

3. A lip protection device as in claim 2 where said oval shaped lip covering member is curved to conform to a user's mouth.

4. A lip protection device as in claim 1 where said lip protection device is molded of a soft plastic material; a sun glass type material.

5. A lip protection device as in claim 4 where said oval shaped lip covering member is curved to conform to a user's mouth.

* * * * *